Oct. 20, 1970 D. S. WHISLER Plant Pat. 2,992
ROSE PLANT
Filed Jan. 17, 1969
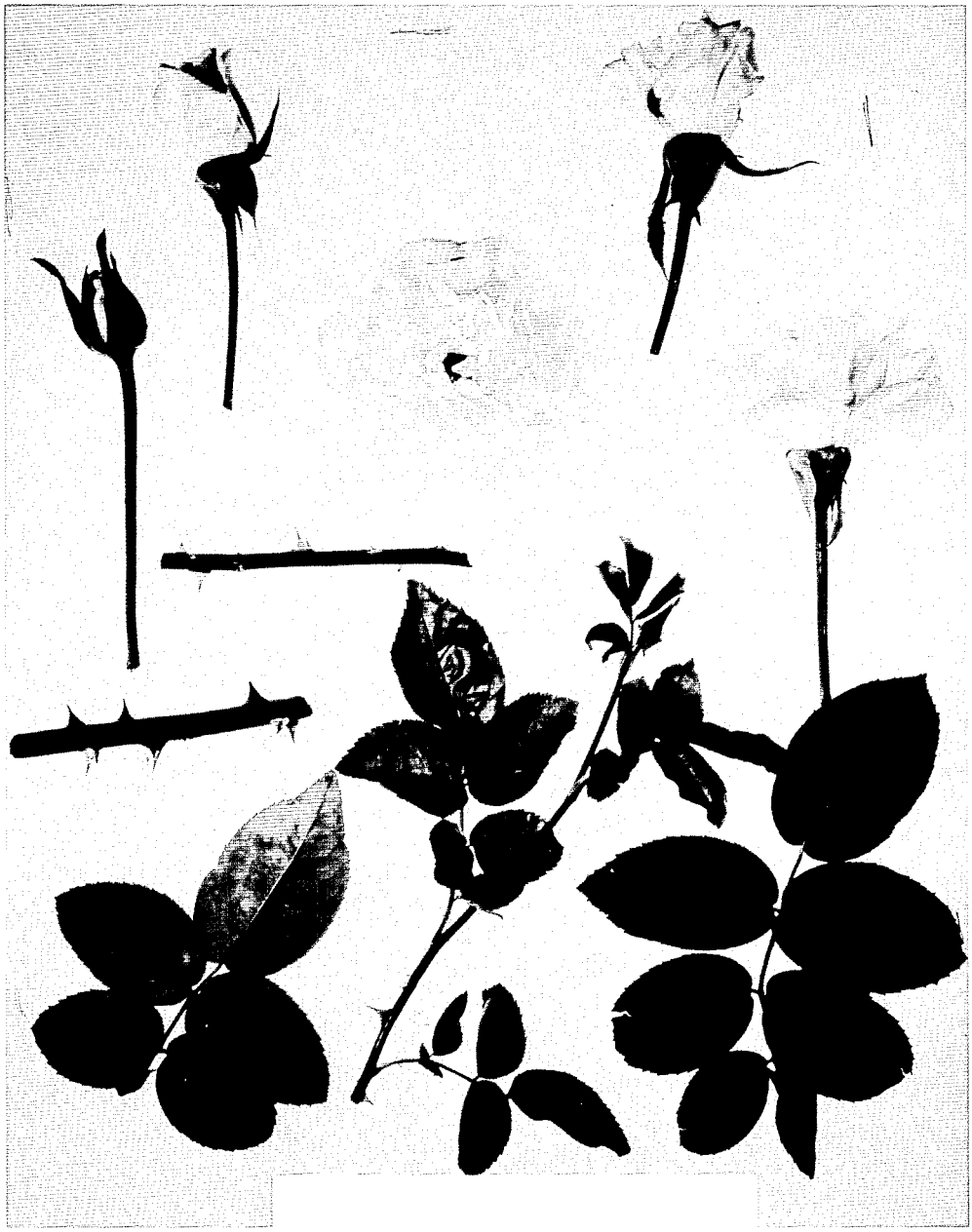
Inventor.
D. S. Whisler
By: Robbins Robb
Attorneys.

United States Patent Office

Plant Pat. 2,992
Patented Oct. 20, 1970

2,992
ROSE PLANT

Dorothy S. Whisler, Shafter, Calif., assignor, by mesne assignments, to Gro-Plant Industries, Inc., Monticello, Fla., a corporation of Florida

Filed Jan. 17, 1969, Ser. No. 792,178
Int. Cl. A01h *5/00*
U.S. Cl. Plt.—15 1 Claim

The present invention relates to a new and distinct variety of rose plant of the Hybrid Tea class, which was originated by me by crossing the rose variety known as "Charlotte Armstrong" (Plant Pat. No. 455—expired) with the rose variety known as "Fred Howard" (Plant Pat. No. 1,006), the former being the seed parent and the latter being the pollen parent.

As the result of this breeding, I have produced a new and improved rose variety which is distinguished from its parents, as well as from all other rose varieties of which I am aware, as evidenced by the following unique combination of characteristics which are outstanding in the new variety.

(1) A neat, vigorous, upright, moderately tall and well-clothed plant habit;

(2) Larger than average foliage which is semi-glossy and medium dark green in color;

(3) Moderate thorniness, with the thorns being slender, almost straight and inclining only slightly downward;

(4) Remarkable bloom abundance and rapid bloom recycle, said blooms being borne singly or in clusters of 2 or 3 to the stem, on strong stems of moderate length;

(5) Ovoid bulbs which open to excellent high-centered blooms which maintain in all stages an elegant regular spiral petal arrangement and even imbrication;

(6) Good flower petalage of from 55 to 65 petals and an almost complete lack of petaloids;

(7) A distinctive and attractive medium yellow bud and opening flower color, finishing to an even creamy yellow color, with both sides of the petals being the same color shade, but with the base of each petal being a deeper yellow color, and the center of the opening blooms having a more intense color effect and giving a very attractive glowing appearance to the flowers;

(8) A very slight tea flower fragrance; and (9) A substantially sterile habit of the flowers, with fewer than average stamens which are grouped regularly around the stigmas.

The principal and significant differences between my new variety and its parents will be apparent from the following comparison:

| Charlotte Armstrong (Seed parent) | Fred Howard (Pollen parent) | This Cultivar |
|---|---|---|
| Cerise rose color with light yellow petal base. | Yellow, orange, and pink blend; bright yellow base. | Even medium Yellow; bright yellow petal base. |
| 25 to 35 petals | 50 to 60 petals | 55 to 65 petals. |
| Long pointed urn-shaped bud. | Ovoid or globular bud. | Ovoid bud. |
| Opening bloom high centered. | Opening bloom high centered. | Opening bloom high-centered. |
| Soon shows stamens though petals may stay up. | Shows stamens as bloom eventually opens flat. | Almost never shows stamens; high-centered; well maintained. |
| Well shaped spiral imbrication. | Opens even; imbrication may become quite irregular. | Very regular spiral imbrication that is well maintained. |
| Long yellow filaments; many average sized anthers. | Short red and yellow filaments; many large anthers. | Intermediate red and yellow filaments; few average sized anthers. |
| Three to five petaloids. | Five to many petaloids. | Usually no petaloids. |
| Upright habit, but somewhat spreading. | Upright habit | Upright habit. |
| Light neck, but occasionally nodding. | Heavy neck | Intermediate neck; never nodding. |

| Charlotte Armstrong (Seed parent) | Fred Howard (Pollen parent) | This Cultivar |
|---|---|---|
| Thorns slender, no curve, slight downward direction; light green on flower stems. | Thorns more robust; moderate downcurve; reddish green on flower stems; many reddish prickles. | Thorns slender, no curve; slight downward direction; light yellow-green on flower stems; very few reddish prickles. |
| Foliage medium large, medium green, semi-glossy, smooth surface. | Foliage dark green; large, dull, deeply veined. | Foliage intermediate in size and color, semi-glossy, intermediate veining. |

My new variety most nearly resembles the rose variety known as "King's Ransom" (Plant Pat. No. 2,103), but is distinctly different therefrom as will be apparent from the following comparison:

| This Cultivar | "King's Ransom" |
|---|---|
| Medium yellow bloom; bright yellow base of petal; same shade both sides of petal; finishing color, creamy ellow. | Medium yellow bloom; bright yellow base of petal; same shade both sides of petal; finishing color, creamy yellow. |
| Bud ovoid | Bud ovoid. |
| Opens to a high-centered bloom; holds spiral conformation throughout bloom life; petals as unfurl, reflex gently. | Begins to open to a high-centered bloom, then tends to quarter in the center, finishes quite irregular; petals may reflex quite sharply. |
| Almost no petaloids | Many petaloids. |
| Few intermediate length filaments, colored red and yellow; average sized anthers, arranged regularly around the stigmas. | Very few short filaments, all yellow; average sized anthers, irregularly placed among the petaloids. |
| Upright habit; well-clothed | Upright habit; well-clothed. |
| Semi-glossy foliage, medium large leaves, medium dark green; stipules straight, turned out much less than 45°. | Glossy foliage, medium large leaves, dark green; stipules sharply turned out. |
| Thorns on flower stems light yellow green, straight, slightly turned down, no curve. | Thorns on flower stems light yellow green, curved downward. |

Asexual reproduction of my new variety of budding, as performed at Shafter, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horti-cultural Colour Chart of the British Colour Council, except where general color terms of ordinary dictionary significance are obvious.

Type: Half-hardy; bush; outdoor; seedling; for cut flowers and for garden decoration.

Class: Hybrid tea.

Breeding: Seedling.

*Seed parent.*—"Charlotte Armstrong."

*Pollen parent.*—"Fred Howard."

Propagation: Holds its distinguishing characteristics through succeeding propagations by budding.

FLOWER

Locality where grown and observed: Shafter, Calif.

Flowers borne: Singly and 2 or 3 to stem; on strong stems of medium length.

Quantity of bloom: Abundant, outdoors.

Continuity: Continuous.

Fragrance: Slight.

*Nature.*—Tea.

Bud:

*Peduncle.*—Medium length; medium caliper; erect; almost smooth; with numerous green hairs. Color—medium green.

*Before calyx breaks.*—Size—medium. Form—pointed oval; with occasional foliaceous appendages on the surface of the bud; with slender, usually entire foliaceous parts extending beyond the tip of the bud equal to ¼ of its length. Color—Scheele's Green, Plate 860/3.

*As calyx breaks.*—Color—Scheele's Green, Plate 860/3.

*As first pedal opens.*—Size—medium. Form—globular. Color—outside: Canary Yellow, Plate 2/3, with base Canary Yellow, Plate 2; inside: Canary Yellow, Plate 2/3, with base Canary Yellow, Plate 2.

*Opening.*—Opens up well.

Bloom:

*Size (when fully open).*—Large; from 4½ inches to 5½ inches.

*Petalage.*—Very double; from 55 to 65 petals; arranged regularly.

*Form.*—High-centered at first and remaining high-centered; petals at first being rolled outward and remaining rolled outward at maturity.

Petals:

*Texture.*—Thick.

*Appearance.*—Inside—Satiny. Outside—velvety.

*Shape.*—Outside—oval. Intermediate—ovate. Inside—obovate.

This description of a newly opened flower was made from a rose grown outdoors during the month of June at Shafter, Calif.:

Color:

*Outer petal.*—Outside surface—Canary Yellow, Plate 2/3. Inside surface—Primrose Yellow, Plate 601/3.

*Intermediate petal.*—Outside surface—Canary Yellow, Plate 2/3. Inside surface—Canary Yellow, Plate 2/3.

*Inner petal.*—Outside surface—Canary Yellow, Plate 2/2. Inside surface—Canary Yellow, Plate 2/2.

This description was made from a rose that was open for three days outdoors during the month of June at Shafter, Calif.:

Color:

*Outer petal.*—Outside surface—Primrose Yellow, Plate 601/3. Inside surface—Primrose Yellow, Plate 601/3.

*Inner petal.*—Outside surface—Canary Yellow, Plate 2/2. Inside surface—Canary Yellow, Plate 2/2.

*General color effect.*—Newly opened flower—Canary Yellow, Plate 2/3. 3-days open—Primrose Yellow, Plate 601/3.

*Behavior.*—Drop off cleanly.

*Flower longevity.*—On bush in garden—5 days or more in June. Cut roses grown outdoors and kept at living-room temperatures—4 or 5 days in June.

REPRODUCTIVE ORGANS

Stamens: Few; regularly arranged about pistils.

Filaments: Medium length; most with anthers.

*Color.*—Reddish yellow.

Anthers: Medium size; open at various times.

*Color.*—Yellow.

Pollen: Sparse.

*Color.*—Lemon.

Pistils: Medium number.

Styles: Even; medium length; medium caliper.

Stigma:

*Color.*—Yellow.

Ovaries: All enclosed in calyx.

Hips: None observed.

Sepals: Permanent; long; spear-shaped.

*Color.*—Scheele's Green, Plate 860/3, covered with white hairs.

Seeds: None observed.

PLANT

Foliage:

*Leaves.*—Compound of 5 leaflets; abundant; moderately glossy.

*Leaflets.*—Base—round. Margin—simple serrate.

*Color.*—Mature—upper surface: moderately dark green; under surface: moderately grey-green. Young—upper surface: moderately green-bronze; under surface: moderately grey-green-bronze.

*Rachis (the supporting stem of the compound leaf).*—Medium caliper. Upper side—smooth. Under side—smooth.

*Stipulses.*—Moderately long; moderately narrow; with moderately long points turning out at an angle of less than 90°.

*Disease resistance.*—Resistant to mildew, as determined by comparison with other varieties grown under comparable conditions at Shafter, Calif.

Growth:

*Habit.*—Upright.

*Growth.*—Moderately vigorous.

*Canes.*—Medium heavy.

*Main stems.*—Color—Green-brown. Thorns—several; long; straight; inclined slightly downward; with narrow base. Prickles—none. Hairs—none.

*Brances.*—Color—bright green. Thorns—several; medium length; straight; with narrow base. Prickles—few. Color—light green. Hairs—several. Color—light green.

*New shoots.*—Color—brigfht green. Thorns—few; long; straight. Prickles—none. Hairs—none.

I claim:

1. A new and distinct variety of rose plant of the hybrid tea class, substantially as herein shown and described, characterized particularly as to novelty by the unique combination of a neat, vigorous, upright, moderately tall and well-clothed plant habit, larger than average foilage which is semi-glossy and medium dark green in color, moderate thorniness, with the thorns being slender, almost straight and inclining only slightly downward, remarkable bloom abundance and rapid bloom re-cycle, said blooms being borne singly or in clusters of 2 or 3 to the stem, on strong stems of moderate length, ovoid buds which open to excellent high-centered blooms which maintain in all stages an elegant regular spiral petal arrangement and even imbrication, good flower petalage of from 55 to 65 petals and an almost complete lack of petaloids, a distinctive and attractive medium yellow bud and opening flower color, finishing to an even creamy yellow color, with both sides of the petals being the same color shade, but with the base of each petal being a deeper yellow color, and the center of the opening blooms having a more intense color effect and giving a very attractive glowing appearance to the flowers, a very slight tea flower fragrance, and a substantially sterile habit of the flowers, with fewer than average stamens which are grouped regularly around the stigmas.

No references cited.

ROBERT E. BAGWILL, Primary Examiner